US012723019B2

(12) United States Patent
Hodges et al.

(10) Patent No.: US 12,723,019 B2
(45) Date of Patent: Sep. 1, 2026

(54) INTERMEDIATES

(71) Applicant: Syngenta Crop Protection AG, Basel (CH)

(72) Inventors: George Robert Hodges, Bracknell (GB); Martin Charles Bowden, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 494 days.

(21) Appl. No.: 18/551,292

(22) PCT Filed: Mar. 23, 2022

(86) PCT No.: PCT/EP2022/057620
§ 371 (c)(1), (2) Date: Sep. 19, 2023

(87) PCT Pub. No.: WO2022/207428
PCT Pub. Date: Oct. 6, 2022

(65) Prior Publication Data

US 2024/0190814 A1 Jun. 13, 2024

(30) Foreign Application Priority Data

Mar. 29, 2021 (GB) .................................... 2104417

(51) Int. Cl.
*C07C 251/20* (2006.01)
*C07C 251/08* (2006.01)

(52) U.S. Cl.
CPC .......... *C07C 251/20* (2013.01); *C07C 251/08* (2013.01)

(58) Field of Classification Search
CPC ........................... C07C 251/20; C07C 251/08
See application file for complete search history.

(56) References Cited

U.S. PATENT DOCUMENTS 4,324,580 A 4/1982 Vogel et al.
5,430,188 A * 7/1995 Bader .................. C07C 213/02 564/214
9,358,532 B2 * 6/2016 Li .................... C07F 9/657154

FOREIGN PATENT DOCUMENTS

EP 3271325 A1 9/2016
WO 2016153374 A1 9/2016

OTHER PUBLICATIONS

GB search report for GB2104417.7. Date of search Sep. 20, 2021.
ISR for PCT/EP2022/057620. Mailed Aug. 1, 2022.

* cited by examiner

*Primary Examiner* — Sikarl A Witherspoon
(74) *Attorney, Agent, or Firm* — R. Kody Jones

(57) ABSTRACT

A compound:

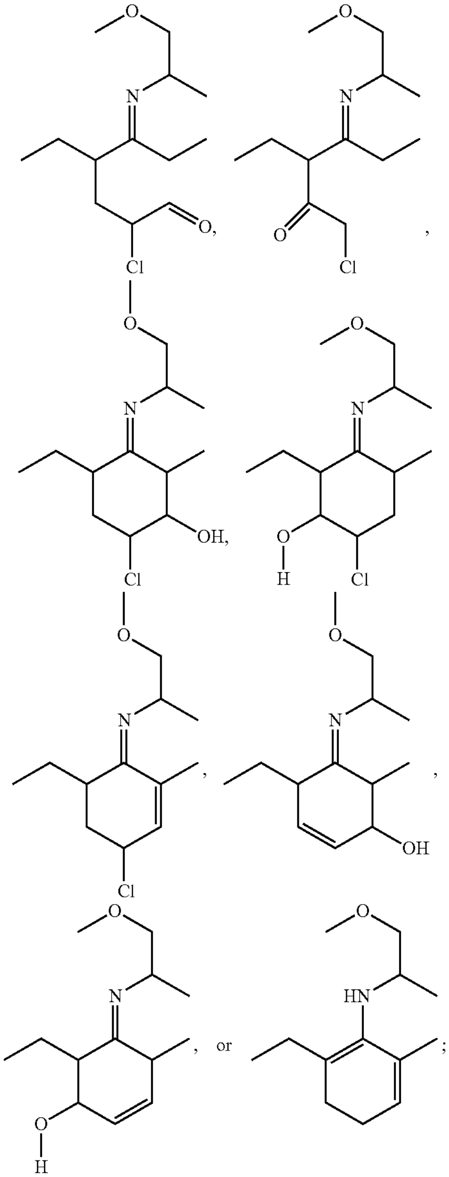

or and double bond regioisomers thereof.

3 Claims, 1 Drawing Sheet

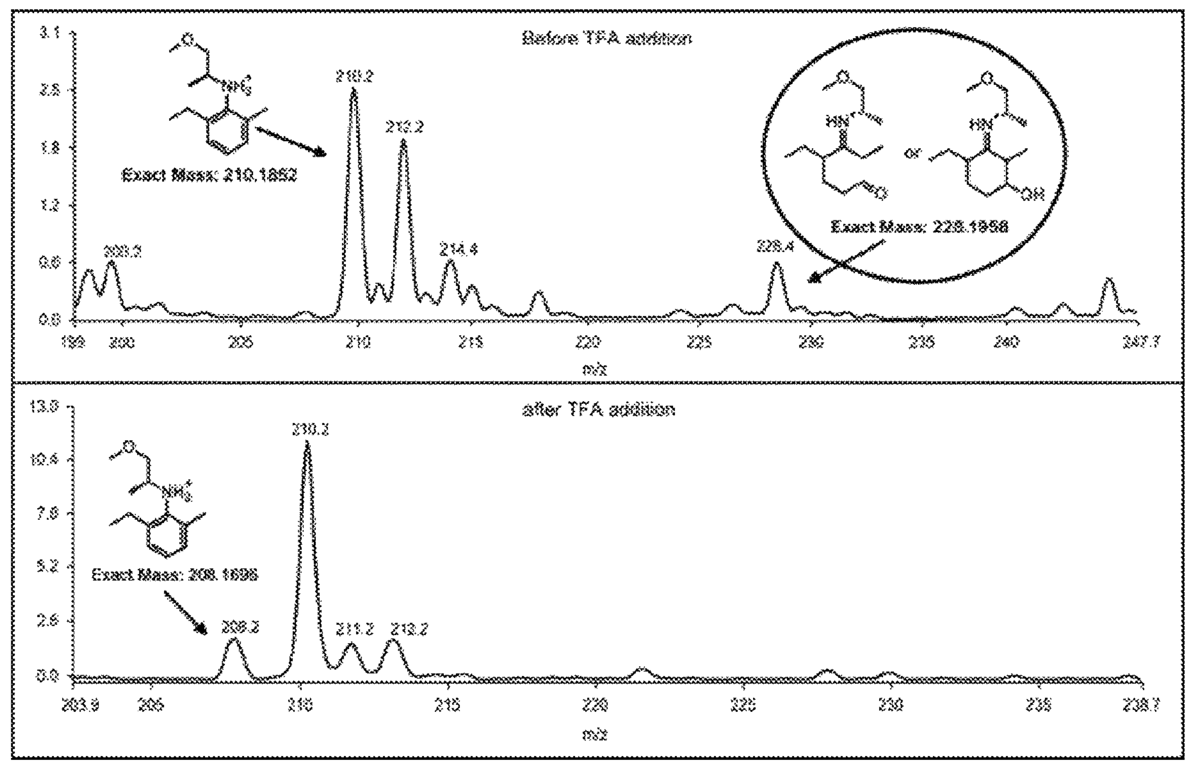
Before TFA addition
Exact Mass: 210.1852
210.2
212.2
214.4
228.4
or
Exact Mass: 228.1958
m/z
after TFA addition
Exact Mass: 208.1696
208.2
210.2
211.2
212.2
m/z

INTERMEDIATES

RELATED APPLICATION INFORMATION

This application is a 371 of International Application No. PCT/EP2022/057620, filed 23 Mar. 2022, which claims priority to GB Application No. 2104417.7, filed 29 Mar. 2021, the contents of which are incorporated herein by reference herein.

The present technology relates to novel intermediates, and isomers thereof.

S-Metolachlor (S-MOC) and metolachlor are part of the chloroacetanilide family of herbicides, used to control grasses and broad-leafed weeds in maize. S-Metolachlor and metolachlor are known to be produced by reacting (S)-NAA or NAA and with chloroacetyl chloride.

The present technology is useful in the production of chemical herbicides S-Metolachlor (S-MOC) and metolachlor. The present invention therefore defines a compound, or double bond regioisomers thereof, as set out in Table 1 below:

TABLE 1

| Compound | Structure |
|---|---|
| 1 | 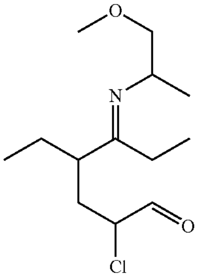 [SMILES: CC/C(=N\C(C)COC)C(CC)CC(Cl)C=O] |
| 2 | 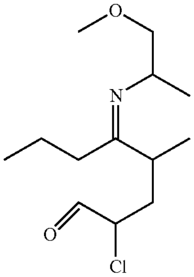 [SMILES: CCC/C(=N/C(C)COC)C(C)CC(Cl)C=O] |
| 3 | 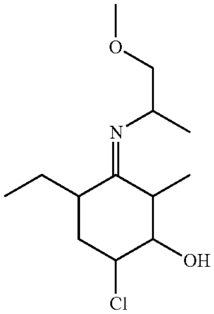 [SMILES: CCC1CC(Cl)C(O)C(C)/C1=N\C(C)COC] |

TABLE 1-continued

| Compound | Structure |
|---|---|
| 4 | 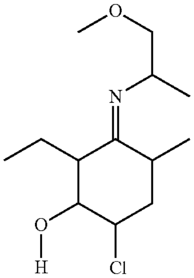 [SMILES: CCC1/C(=N/C(C)COC)C(C)CC(Cl)C1O] |
| 5 | 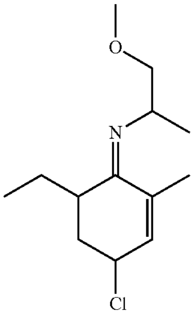 [SMILES: CCC1CC(Cl)C=C(C)/C1=N\C(C)COC] |
| 6 | 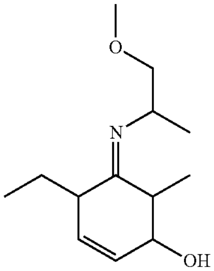 [SMILES: CCC1C=CC(O)C(C)/C1=N\C(C)COC] |
| 7 | 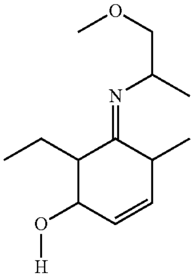 [SMILES: CCC1/C(=N/C(C)COC)C(C)C=CC1O] |
| 8 | 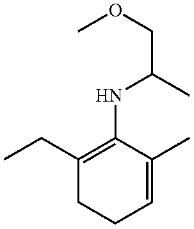 |

The present invention also defines a compound, or double bond regioisomers thereof, as set out in Table 2 below:

TABLE 2
| Compound | Structure |
|---|---|
| 1a | 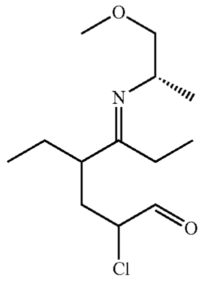 [SMILES: CC/C(=N\[C@@H](C)COC)C(CC)CC(Cl)C=O] |
| 2a | 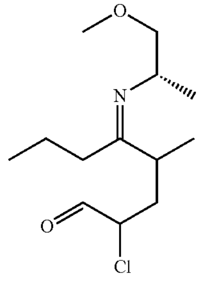 [SMILES: CCC/C(=N/[C@@H](C)COC)C(C)CC(Cl)C=O] |
| 3a | 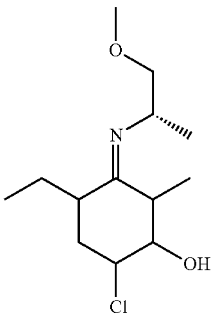 [SMILES: CCC1CC(Cl)C(O)C(C)/C1=N\[C@@H](C)COC] |
| 4a | 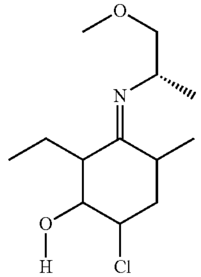 [SMILES: CCC1/C(=N/[C@@H](C)COC)C(C)CC(Cl)C1O] |
TABLE 2-continued
| Compound | Structure |
|---|---|
| 5a | 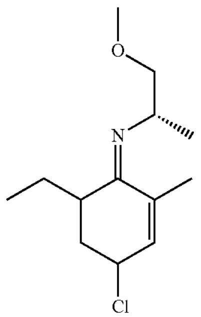 [SMILES: CCC1CC(Cl)C=C(C)/C1=N\[C@@H](C)COC] |
| 6a | 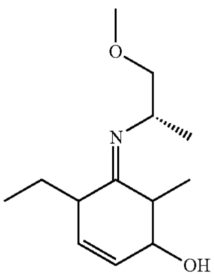 [SMILES: CCC1C=CC(O)C(C)/C1=N\[C@@H](C)COC] |
| 7a | 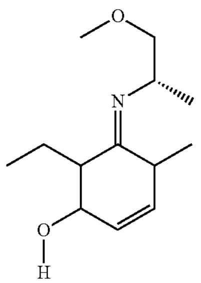 [SMILES: CCC1/C(=N/[C@@H](C)COC)C(C)C=CC1O] |
| 8a | 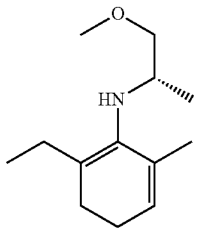 |
Production of (S)-NAA using the novel imine of the present technology is shown below in Schemes 1 through 4:

Scheme 1
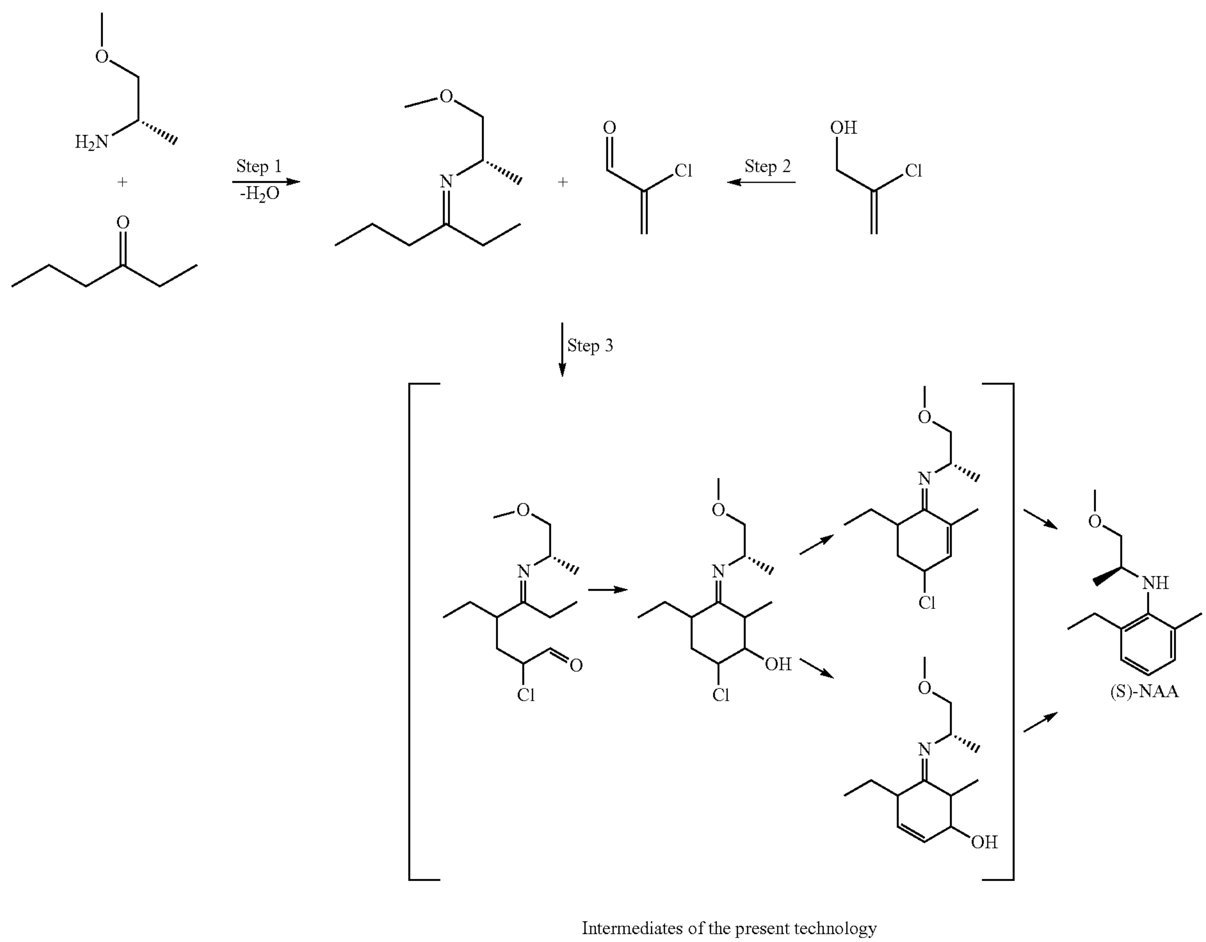
(S)-NAA
Intermediates of the present technology
Scheme 2
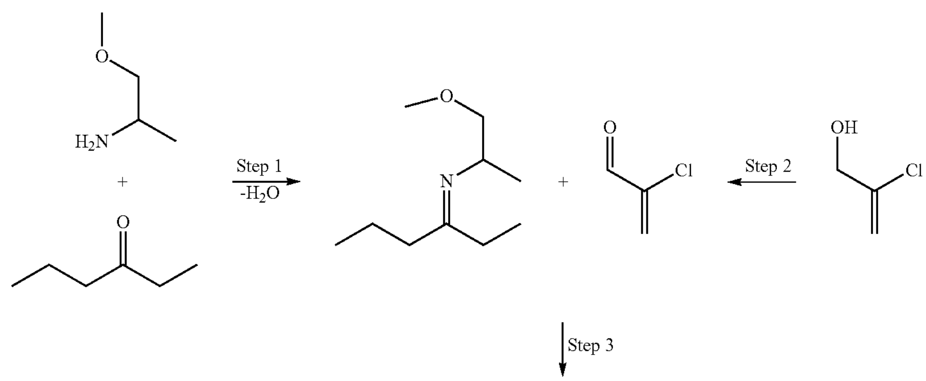

-continued

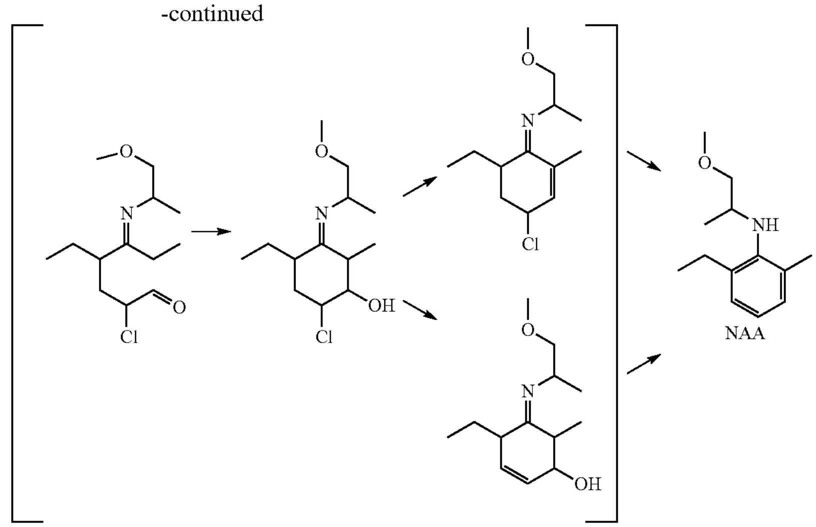

Intermediates of the present technology

In the case of Schemes 1 and 2, the reaction may proceed to form the alternate regioisomers, i.e., compounds 2, 4 and 7 or compounds 2a, 4a and 7a as defined above.

Scheme 3

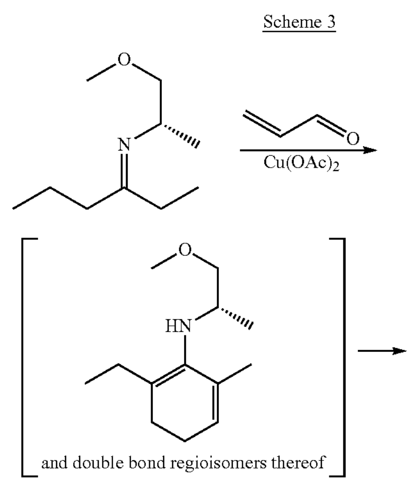

Intermediates of the present technology

Scheme 4

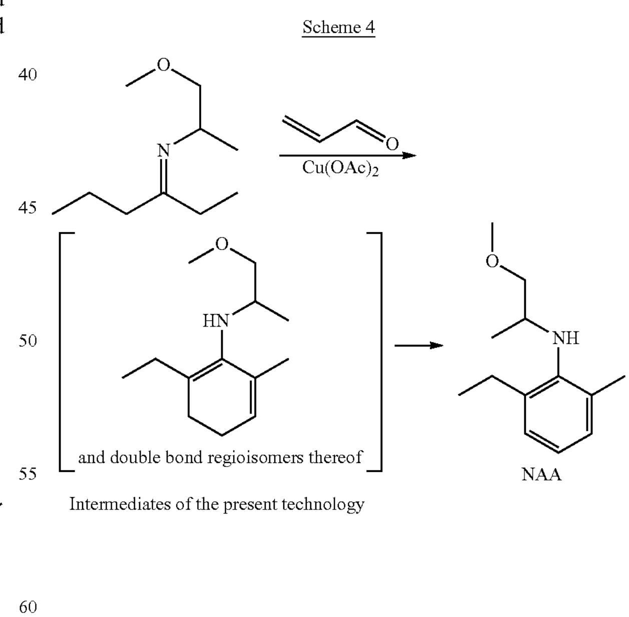

Intermediates of the present technology

In an alternative embodiment, the reaction may proceed from the acrolein dimethylacetal. This is shown in Scheme 5 (and similarly applies to the racemic mixture):

Scheme 5
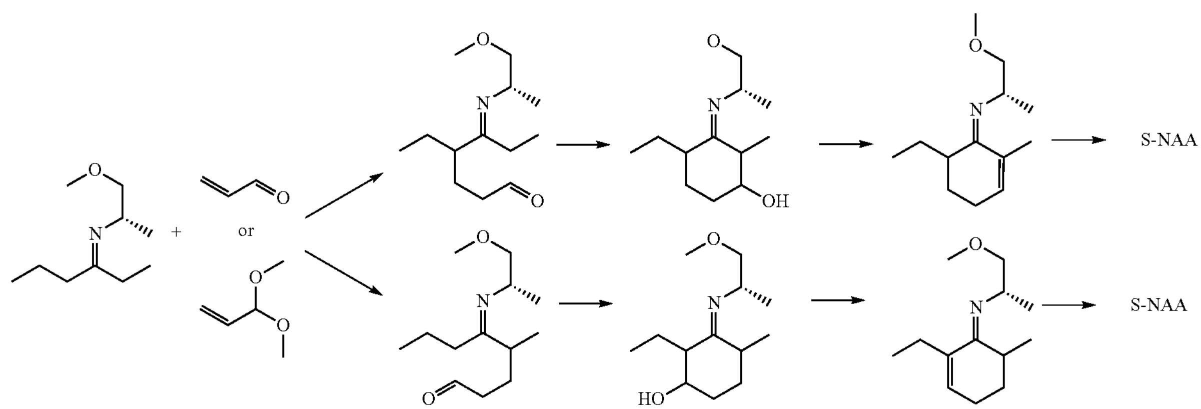
The present invention therefore also defines compounds as set out in Table 3:
TABLE 3
| Compound | Structure |
|---|---|
| 9 | 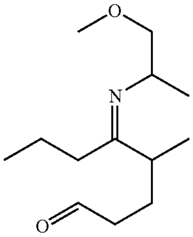 [SMILES: CCC/C(=N/C(C)COC)C(C)CCC=O] |
| 9a | 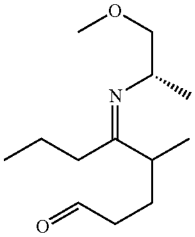 [SMILES: CCC/C(=N/[C@@H](C)COC)C(C)CCC=O] |
| 10 | 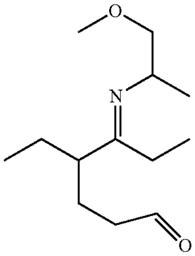 [SMILES: CC/C(=N\C(C)COC)C(CC)CCC=O] |
| 10a | 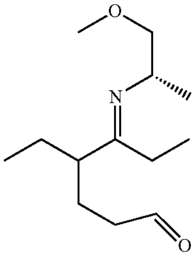 [SMILES: CC/C(=N\[C@@H](C)COC)C(CC)CCC=O] |
TABLE 3-continued
| Compound | Structure |
|---|---|
| 11 | 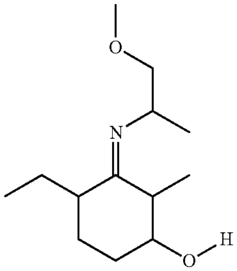 [SMILES: CCC1CCC(O)C(C)/C1=N\C(C)COC] |
| 11a | 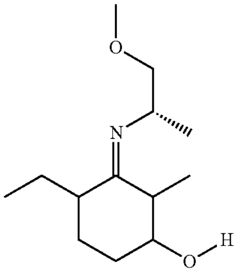 [SMILES: CCC1CCC(O)C(C)/C1=N\[C@@H](C)COC] |
| 12 | 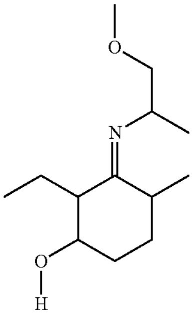 [SMILES: CCC1/C(=N/C(C)COC)C(C)CCC1O] |

TABLE 3-continued

| Compound | Structure |
|---|---|
| 12a | 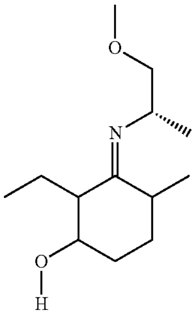 [SMILES: CCC1/C(=N/[C@@H](C)COC)C(C)CCC1O] |

The invention is described by the following non-limiting Examples.

EXAMPLES

Experiment 1

The intermediates of the present technology were created during the production of NAA and S-(NAA) in the reaction shown below ((S)-NAA shown):

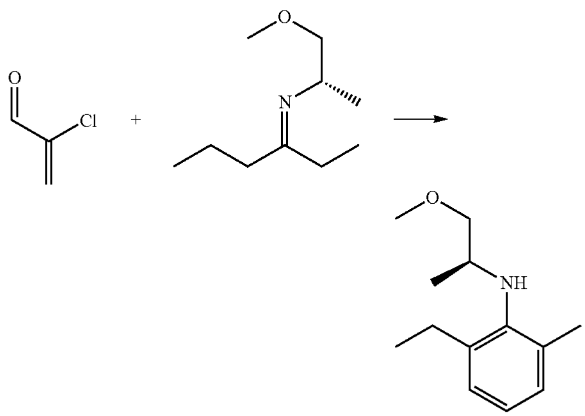

An oven-dried round bottom flask was equipped with nitrogen inlet and magnetic follower. 1,3,5-trimethoxybenzene (10 mol %) charged as internal standard.

Activated molecular sieves (5% w/v) were charged to the reactor. Imine (15 mmol) was added to anhydrous toluene (dried over molecular sieves, 20 mL), mixed and the solution then syringed into the reactor. Chloroacrolein (15 mmol, 1.0 eq) was added to anhydrous toluene and the solution syringed into the reactor. Acetic acid (1.0 eq) was added dropwise over ca. 30 seconds and the reaction then heated to 95° C. (external temperature) on a Drysyn heating block and held with stirring for 3 hr.

The reaction was cooled to room temperature and concentrated under vacuum (35 mbar, 30° C.). Analysis by GC and $^1H$ NMR showed the desired product S-NAA [S-2-Ethyl-N-(2-methoxy-1-methyl-ethyl)-6-methyl-aniline] had been formed with >99% e.r, in 12% yield (strength 9%).

Experiment 2

The intermediates of the present technology were created during the production of NAA and S-(NAA) in the reaction shown below ((S)-NAA shown):

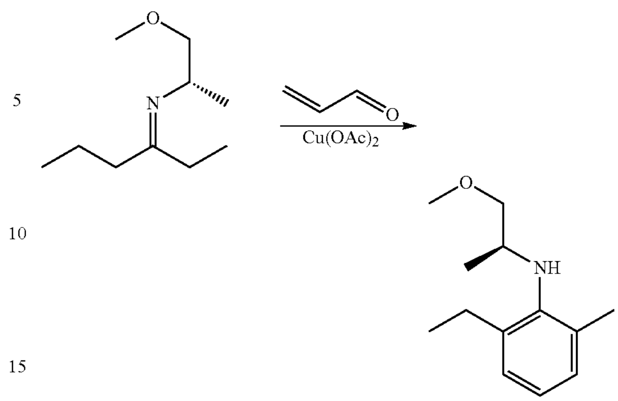

A 100 mL round bottomed flask was equipped with magnetic follower and condenser. To this was added (S)—N-(2-Methoxy-1-methyl-ethyl)hexan-3-imine) (227.6 mg, 1.33 mmol, 1 eq) as a solution in Toluene (6 mL), followed by acrolein (74.5 mg, 88.9 uL, 1.33 mmol, 1 eq). $Cu(OAc)_2$ (265.5 mg, 1.33 mmol, 1 eq) was added in one portion, followed by an additional 6 mL of toluene. The mixture was warmed to ~25° C. internal temperature before the dropwise introduction of trifluoroacetic acid (151.7 mg, 102.9 uL, 1.33 mmol, 1 eq). The reaction was then heated to 110° C. (internal temperature) (~140° C. heating block temperature) maintained at this temperature for 3 hours.

The reaction mixture was allowed to cool to ambient, then concentrated in vacuo. The product (S)-NAA [S-2-Ethyl-N-(2-methoxy-1-methyl-ethyl)-6-methyl-aniline] was formed in 60% conversion, and chiral analysis showed desired S-NAA product to have been formed with >99% e.r.

Experiment 3

FIG. 1 shows MS spectra demonstrating the formation of compounds 10(a) and/or 11(a) as defined above proceeding according to the scheme:

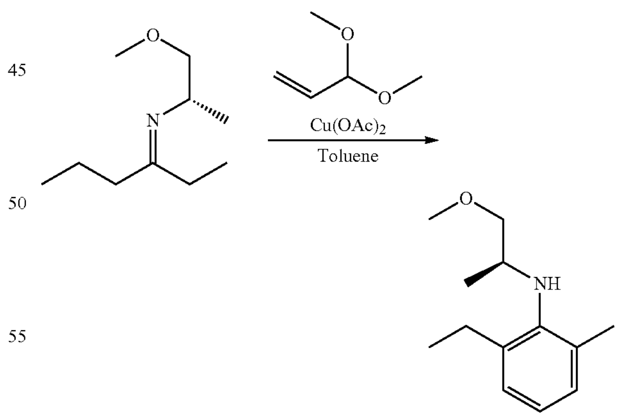

A three-neck round bottomed flask was equipped with magnetic stirrer, condenser and peristaltic pump which allows small samples to be taken and, after dilution in acetonitrile/0.1% formic acid, analysed by mass spectrometry.

(a) (S)—N-(2-Methoxy-1-methyl-ethyl)hexan-3-imine (485 mg, 93% strength, 2.6 mmol) was diluted in toluene (10 ml) and charged into the reactor and stirring started. After ca. 10 minutes, acrolein dimethyl acetal (269 mg, 2.6 mmol) was charged to the vessel as a solution in toluene (6 ml), and conditions held for ca. 8 minutes. $Cu(OAc)_2$ (525 mg, 2.9 mmol) was charged to the vessel followed by TFA (0.2 mL, 2.6 mmol) and heating initiated. The reaction was then held at reflux for 3 h. Analysis by mass spectroscopy gave spectral data consistent with diene compound 8a.

(b) (S)—N-(2-Methoxy-1-methyl-ethyl)hexan-3-imine (485 mg, 93% strength, 2.6 mmol) was diluted in toluene (16 ml) and charged into the reactor. Molecular sieves (5 g) were added, and the mixture heated to reflux with stirring. After 10-20 minutes, acrolein dimethyl acetal (269 mg, 2.6 mmol) in toluene was charged to the vessel toluene, and the mixture held for 30-80 minutes. TFA (0.2 mL, 2.6 mmol) was charged and the reaction held for 40 minutes. Analysis by mass spectroscopy gave spectral data consistent with the alcohol or aldehyde compounds 9a, 10a, 11a, 12a and the diene compound 8a.

The invention is defined by the claims:

The invention claimed is:

1. A compound:

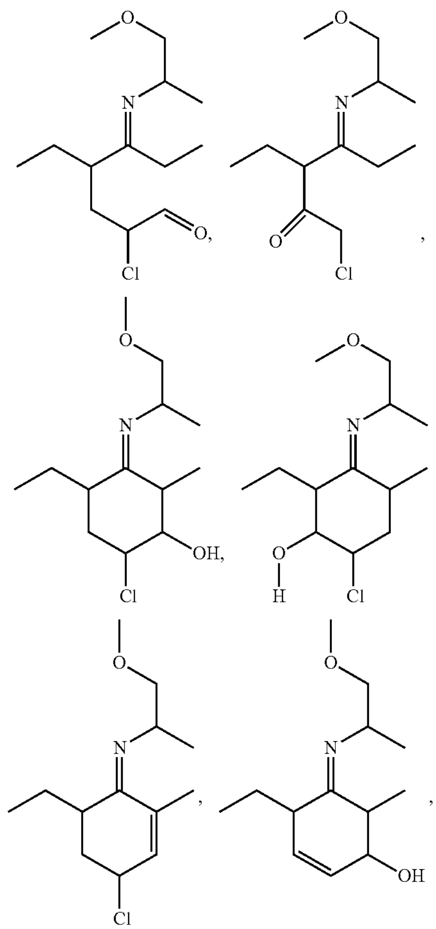

-continued

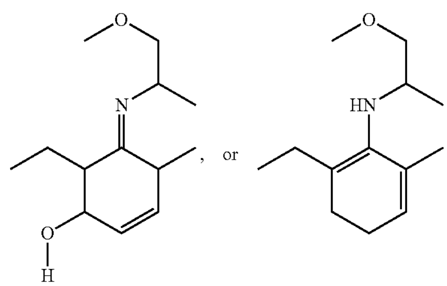

and double bond regioisomers thereof.

2. A compound according to claim 1 selected from:

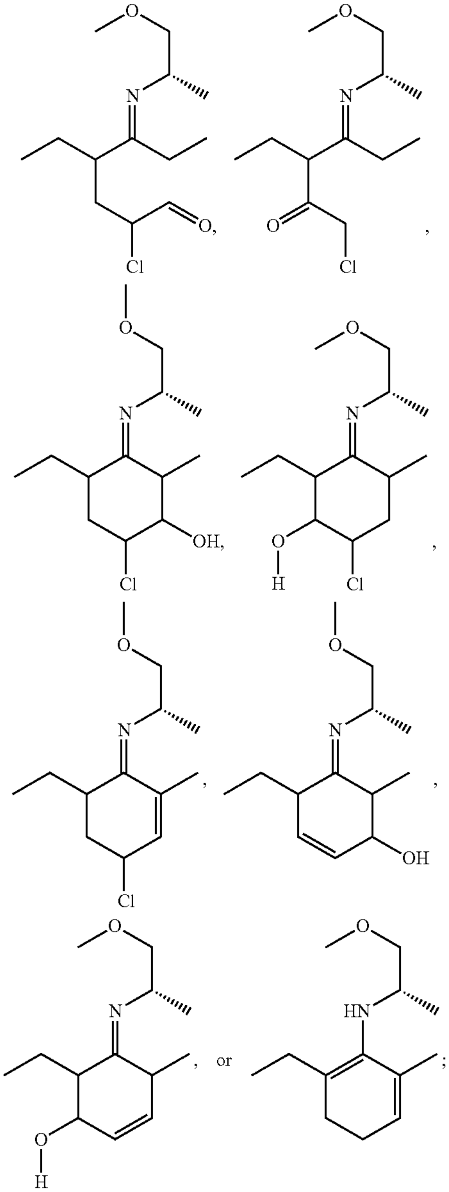

and double bond regioisomers thereof.

3. A compound selected from:
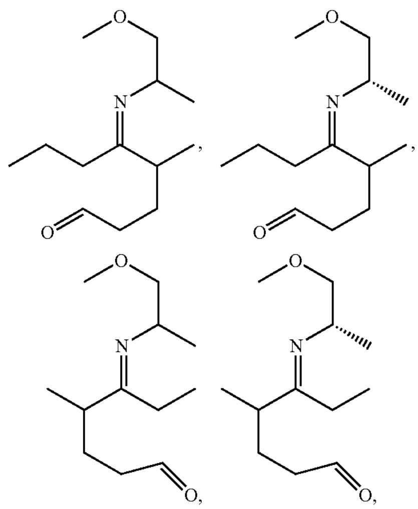
-continued
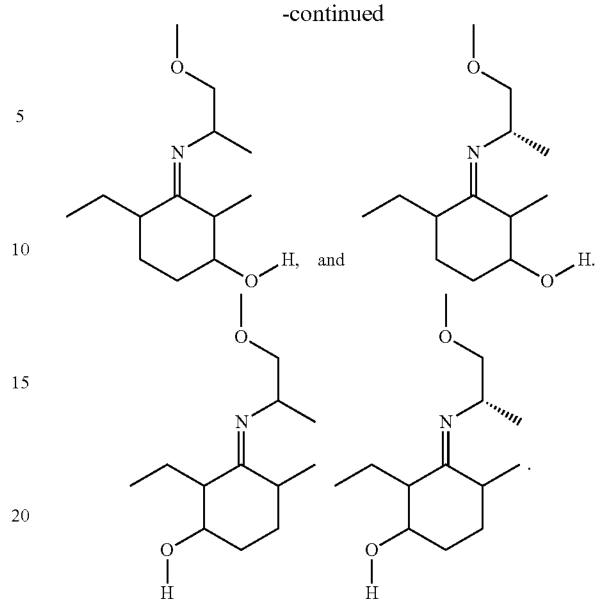
* * * * *